(12) United States Patent
Kulik et al.

(10) Patent No.: US 12,186,516 B2
(45) Date of Patent: Jan. 7, 2025

(54) METHOD AND DEVICE FOR PRODUCING MICRONEEDLES

(71) Applicant: LTS Lohmann Therapie-Systeme AG, Andernach (DE)

(72) Inventors: Michael Kulik, Urmitz (DE); Andreas Hennig, Messstetten (DE)

(73) Assignee: LTS Lohmann Therapie-Systeme AG, Andernach (DE)

( * ) Notice: Subject to any disclaimer, the term of this patent is extended or adjusted under 35 U.S.C. 154(b) by 801 days.

(21) Appl. No.: 17/312,504

(22) PCT Filed: Dec. 4, 2019

(86) PCT No.: PCT/EP2019/083717
§ 371 (c)(1),
(2) Date: Jun. 10, 2021

(87) PCT Pub. No.: WO2020/120262
PCT Pub. Date: Jun. 18, 2020

(65) Prior Publication Data
US 2022/0062604 A1    Mar. 3, 2022

(30) Foreign Application Priority Data

Dec. 11, 2018 (DE) .......................... 102018009594.1

(51) Int. Cl.
*A61M 37/00* (2006.01)
*B29C 39/02* (2006.01)
(Continued)

(52) U.S. Cl.
CPC ....... *A61M 37/0015* (2013.01); *B29C 39/026* (2013.01); *B29C 39/24* (2013.01);
(Continued)

(58) Field of Classification Search
CPC ...... A61M 37/0015; A61M 2037/0046; A61M 2037/0053; B29C 39/026; B29C 39/24;
(Continued)

(56) References Cited

U.S. PATENT DOCUMENTS 8,603,384 B2   12/2013   Lüttge et al.
9,114,238 B2   8/2015    Singh et al.
(Continued)

FOREIGN PATENT DOCUMENTS

CA    2696956 A1   4/2011
CN    1993156 A    7/2007
(Continued)

*Primary Examiner* — Amber R Stiles
(74) *Attorney, Agent, or Firm* — The Webb Law Firm

(57) ABSTRACT

The present disclosure relates to a method for producing microneedle arrays in a mold, including a plurality of receptacles that taper from an upper base surface to a lower tip surface, where a first component is fed into at least two receptacles through a feed opening that is spaced apart from the base surface, where the receptacles are filled with an additional component from above the feed opening, where the fillings of at least said two receptacles, which fillings are formed of at least the first component and the additional component, are connected to one another above the base surfaces, and where after the first component and the additional component have solidified, the microneedle array comprising the fillings that have solidified to form needles is removed from the mold.

10 Claims, 5 Drawing Sheets

(51) Int. Cl.
*B29C 39/24* (2006.01)
*B29C 39/26* (2006.01)
*B29L 31/00* (2006.01)

(52) U.S. Cl.
CPC ..... *B29C 39/26* (2013.01); *A61M 2037/0046* (2013.01); *A61M 2037/0053* (2013.01); *B29L 2031/7544* (2013.01)

(58) Field of Classification Search
CPC .................. B29C 39/26; B29C 43/203; B29C 2043/3205; B29C 43/021; B29C 43/36; B29C 2043/026; B29L 2031/7544; B29L 2031/753; B29L 2031/756
See application file for complete search history.

(56) References Cited

U.S. PATENT DOCUMENTS

| | | | |
|---|---|---|---|
| 9,381,680 B2 | 7/2016 | Oh et al. | |
| 9,566,423 B2 | 2/2017 | Ueno et al. | |
| 10,828,478 B2 | 11/2020 | Mcallister et al. | |
| 2010/0305516 A1 | 12/2010 | Xu et al. | |
| 2015/0238434 A1 | 8/2015 | Yoshida et al. | |
| 2016/0136408 A1* | 5/2016 | Kato | B29C 39/003 604/173 |
| 2017/0333342 A1 | 11/2017 | Wakamatsu | |
| 2020/0261708 A1* | 8/2020 | Chang | B29C 39/26 |

FOREIGN PATENT DOCUMENTS

| | | |
|---|---|---|
| CN | 103691054 A | 4/2014 |
| CN | 106232159 A | 12/2016 |
| EP | 2664323 A1 | 11/2013 |
| EP | 3248593 B1 | 2/2019 |
| JP | 2011206178 A | 10/2011 |
| JP | 2017143963 A | 8/2017 |
| KR | 1020170135773 A | 12/2017 |
| WO | 2014181674 A1 | 11/2014 |

* cited by examiner

METHOD AND DEVICE FOR PRODUCING MICRONEEDLES

CROSS-REFERENCE TO RELATED APPLICATIONS

This application is the United States national phase of International Application No. PCT/EP2019/083717 filed Dec. 4, 2019, and claims priority to German Patent Application No. 10 2018 00 9594.1 filed Dec. 11, 2018, the disclosures of which are hereby incorporated by reference in their entirety.

BACKGROUND OF THE DISCLOSURE

Field Of The Disclosure

The invention relates to a method for producing microneedle arrays in a mold which has a plurality of receptacles that taper from an upper base surface to a lower tip surface, a device for producing microneedle arrays by means of such a method with a mold, and a microneedle array having a plurality of needles that taper from a needle connection cross-section to a smallest end surface.

Description of Related Art

Such a method, a device and a microneedle array produced therewith are known from EP 2 664 323 A1. Here, a solution containing a medication and a solvent is filled into a die. In order to avoid air bubbles, said filling is carried out by means of positive pressure of the solution or negative pressure of the environment.

SUMMARY OF THE DISCLOSURE

The object of the present invention is to ensure sufficient pharmaceutical quality in large-scale production and to allow for a large quantity of microneedle arrays.

This object is achieved with the features of the main claim. A first component is fed into at least two receptacles through a feed opening that is spaced apart from the base surface. Said receptacles are filled with an additional component from above the feed opening. The fillings of at least said two receptacles, which fillings are formed of the first component and the additional component, are connected to one another above the base surfaces. Furthermore, after the first component and the additional component have solidified, the microneedle array comprising the fillings that have solidified to form needles is removed from the mold.

The mold used in said method has a plurality of receptacles that taper from an upper base surface to a lower tip surface. Each receptacle has a feed opening that is spaced apart from the base surface.

In the microneedle array the needles are connected to a support plate in the needle cross-section. Furthermore, the area adjoining the smallest end surface consists of the solidified first component.

The microneedle array is produced in a mold which has a plurality of receptacles that taper from top to bottom. Said receptacles have an inner shell surface connecting an upper base surface and a lower tip surface. Each receptacle has at least one feed opening that is arranged on the shell surface or in the tip surface. Said feed opening can be formed in a closable manner.

The mold can be filled sequentially in at least two method steps during the production of the microarray. A first component, e.g. an active ingredient, a component containing an active ingredient, etc., is introduced into the receptacle through the feed opening. Furthermore, a second component, e.g. a filling, is introduced into the receptacle, for example. Here, first the first and then the second component can be fed. It is also possible to feed both components at the same time. For example, highly viscous components, laminates, powders, etc. can be fed.

The additional components are introduced from the base surface or from a filling opening above the feed opening. Said filling opening is then located between the base surface and the feed opening. The fillings of at least two receptacles are connected to each other above the base surface. Here, the second component or another material can be used. The fillings of the receptacles consisting of at least the first component and the second component are solidified or solidify. It is also possible to solidify the individual components one after another. For example, they are dried by reducing the moisture content. The individual fillings solidify into individual rigid needles. The microneedle array with the needles connected to each other above the base surfaces can then be removed from the mold and applied.

Optionally, the microneedle array can also be produced of more than two components. The second component, which is free of active ingredients, for example, can be used cost-effectively for a wide range of products regardless of the material of the tips, e.g. a mixture of active ingredients and auxiliaries.

The microneedle array consists of at least two components, wherein the tips of the conical needles consists of the solidified first component which is a component containing an active ingredient, for example. Said tips have a circular end surface, for example. Upon application, e.g. on the skin of a patient, the rigid and break-proof needles penetrate the skin of the patient, wherein the tips reach the skin areas below the callus. Optionally, the tips may dissolve during active ingredient delivery. The tips and/or the base of the needles may include one or more substances provided for therapeutic and/or diagnostic application.

Further particularities of the invention result from the subclaims and the following descriptions of schematically illustrated exemplary embodiments.

BRIEF DESCRIPTION OF THE DRAWINGS

FIGS. 1 and 2 show a mold (21), e.g. a casting mold (21), for the production of microneedle arrays (61). In this exemplary embodiment, the mold (21) is produced of a cylindric body. The body of the mold (21) can also be cuboid, cubical, trapezoidal, ellipsoidal, etc. The mold (21) can be produced of an austenitic steel, a thermoplastic or thermoset material, etc. In the illustration of FIGS. 1 and 2, the mold (21) has a circular top surface (22) lying in a plane and a flat bottom surface (23) lying parallel to the top surface. An outer shell surface (24) connects the top surface (22) to the bottom surface (23). The mold (21) has a plurality of receptacles (25). In this exemplary embodiment, said receptacles (25) are formed as apertures (25) that connect the top surface (22) to the bottom surface (23). In the exemplary embodiment, 10 apertures (25) are illustrated for simplification. For example, the mold (21) can have 600 to 700 receptacles (25) per subbase area of 10 square millimeters.

Figure 1:
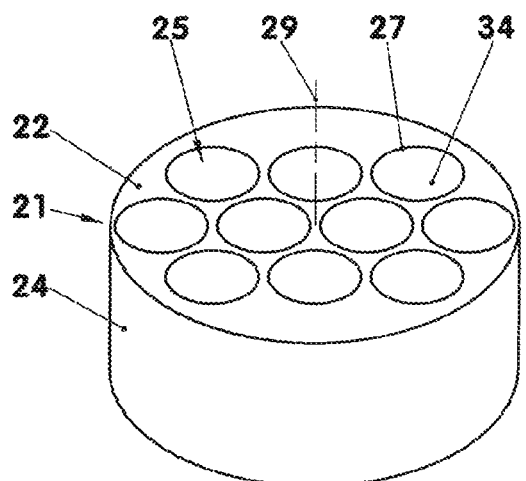
FIG. 1 illustrates an isometric view of an embodiment of the mold.
Figure 2:
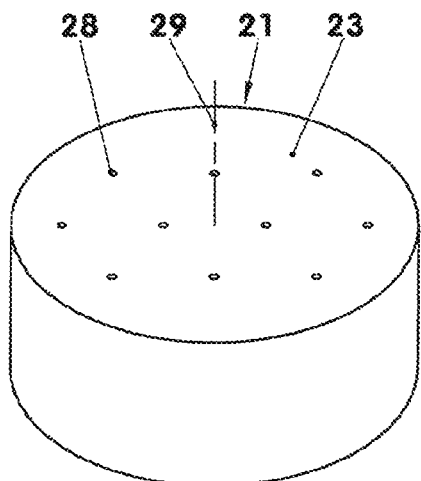
FIG. 2 illustrates a bottom view of the isometric view of FIG. 1.

The mold (21) can also consist of several overlying discs that are centered to each other. The individual discs can be joined together in a detachable or non-detachable manner. The receptacles (25) then penetrate several or all discs, for example.

In the illustrated exemplary embodiment, the individual receptacle (25) has a center line (26) being normal to the top surface (22) and the bottom surface (23). The receptacle (25) tapers in a frustoconical manner from the top surface (22) to the bottom surface (23). The inner shell surface (34) of the receptacle (25) has, for example, a circular cross-section on each point of the center line. The base surface (27) lying in the plane of the top surface (22) as well as the tip surface (28) lying in the plane of the bottom surface (23) of the receptacle (25) are formed in a circular manner, for example. The center line (26) connects the centers of these two circular areas.

The base surface (27) and/or the tip surface (28) may have a shape differing from the circular form. For example, both surfaces may have a square, triangular, elliptical, etc. cross-section. For example, the wall limiting the individual receptacle (25) then has the shape of a truncated pyramid shell surface, a truncated cone portion differing from the circular truncated cone, etc. A transition, for example from a truncated pyramidal portion to a truncated portion is also possible. The individual receptacle (25) can also comprise a portion adjoining the top surface (22) and having a constant cross-section. For example, said portion can be cylindrical, triangular, square, rectangular, hexagonal, etc.

The center line (26) can enclose an angle different from the right angle with the top surface (22) and/or the bottom surface (23). The truncated cone is then formed obliquely, for example. It is also possible to arrange the base surface (27) and the tip surface (28) non-parallel to each other. The receptacles (25) can be in alignment, e.g. they can comprise center lines (26) that are parallel to each other.

Figure 3:
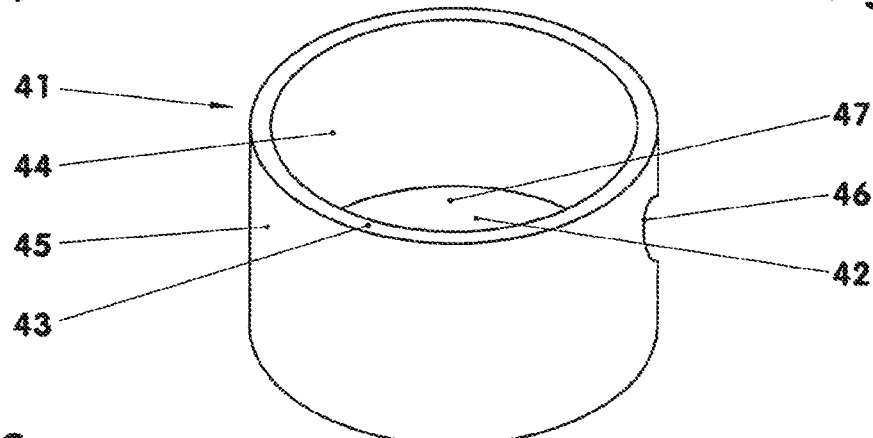
FIG. 3 illustrates an isometric view subshell.

In FIG. 3, a subshell (41) is illustrated. The subshell (41) has a disc-shaped bottom (42) being limited by an annular edge (43). For example, the height of the edge (43) is smaller than the height of the mold (21) in a direction normal to the top surface (22). In this illustration, the edge (43) has an inner surface (44) formed in the manner of a cylindrical shell, and an outer surface (45) being coaxial to the inner surface (44). The inner diameter of the edge (43) is larger than the outer diameter of the mold (21) by a few tenths of a millimeter, for example. In a cuboid design of the mold (21) the edge (43) formed to be rectangular. In this case, the edge (43) also surrounds the mold (21), for example with the mentioned distance. The subshell (41) illustrated in FIG. 3 has a filling connection (46) that is arranged in the edge (43). The filling connection (46) can also be arranged in the bottom (42). The filling connection (46) can be configured to be closable. It is also possible to form the subshell (41) with a closable filling connection (46) in the edge (43) as well as with a closable filling connection (46) in the bottom (42).

Figure 4:
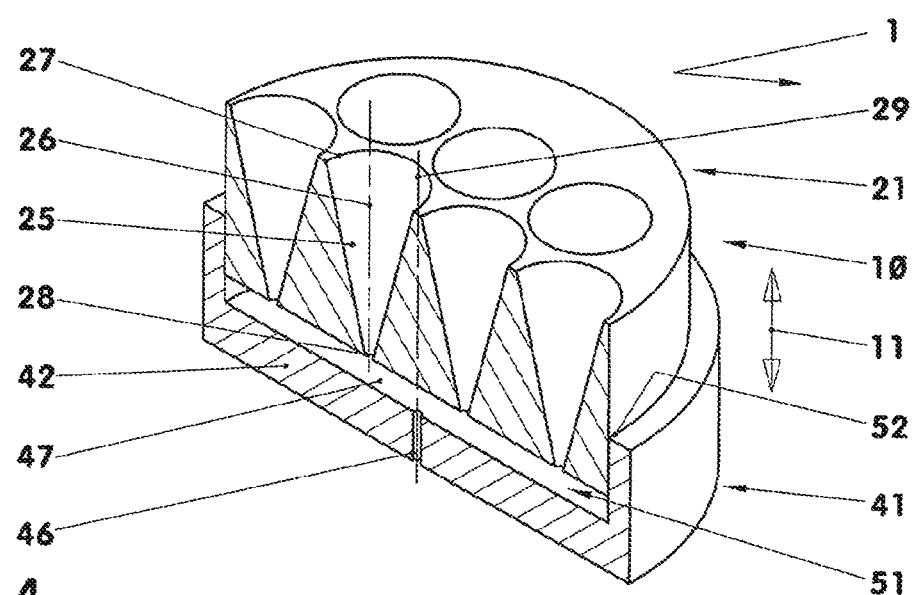
FIG. 4 illustrates an isometric cross-sectional view of an embodiment of the device before filling.

FIG. 4 shows a device (10) with a mold (21) and a subshell (41) in an isometric sectional view. A mold (21) is inserted into the subshell (41). The section plane passes through the center lines (26) of four receptacles (25) and through the common central axis (29) of the mold (21) and the subshell (41). The top surface (22) of the mold (21) with the base surfaces (27) of the receptacles (25) is directed upwards and the bottom surface (23) is oriented towards the bottom (42) of the subshell (41).

In this illustration of FIG. 4, the edge (43) of the subshell (41) encompasses the lower area of the shell surface (24) of the mold (21). The bottom (42) of the subshell (41) is spaced by a feed chamber (51) from the bottom surface (23) of the mold (21). The feed chamber (51) is limited by the subshell (41) and the bottom surface (23). Here, the bottom (42) is parallel to the plane of the bottom surface (23). For example, the height of the feed chamber (51) oriented in the height direction (11) is less than five millimeters. The annular gap (52) between the mold (21) and the subshell (41) can be sealed.

In this example, the filling connection (46) is arranged in the middle of the bottom (42). The filling connection (46) passes through the bottom (42) and connects the feed chamber (51) to the environment (1) in the illustration of FIG. 1. The filling connection (46) can comprise an inner thread. Here, e.g. a container, a syringe, a pressure connection, etc. can be screwed on the exterior of the bottom (42).

The mold (21) and the subshell (41) are movable relative to each other, e.g. displaceable. In the exemplary embodiment, they are adjustable to each other in height direction (11). The feed chamber (51) thus has a variable size. In this exemplary embodiment, the volume of the feed chamber (51) is e.g. controllable by the stroke of the subshell (41) relative to the mold (21) in height direction (11). In the illustration of FIG. 4, the feed chamber (51) has its maximum operating volume. The minimum operating volume of the feed chamber (51) is achieved if the bottom (42) of the subshell (41) abuts against the bottom surface (23) of the mold (21), see FIG. 8. The bottom (42) then closes the receptacle (25) of the mold (21) on the side of the tip surfaces (28). The subshell (41) is now in a second operating position relative to the mold (21). It is also possible that the subshell (41) closes several but not all tip surfaces (28).

Figure 5:
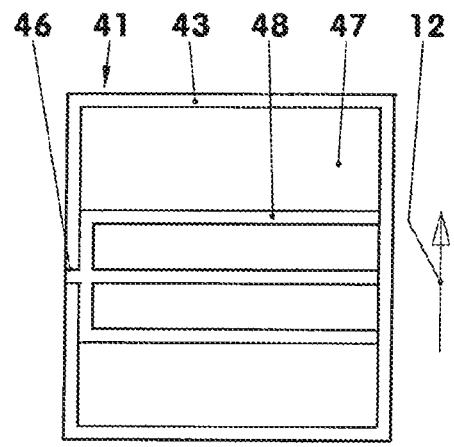
FIG. 5 illustrates a cross-sectional view of an embodiment of the subshell with impressed channels.
Figure 6:
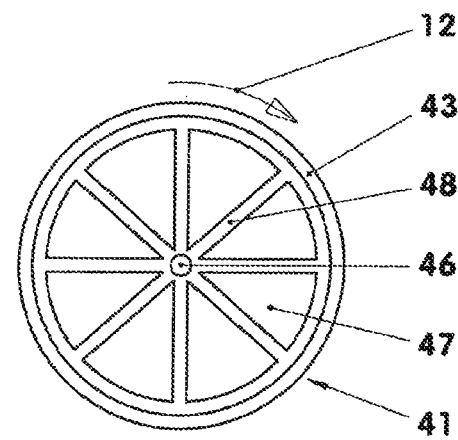
FIG. 6 illustrates a cross-sectional view of an embodiment of the subshell with impressed radial channels.

The device (10) can also be configured such that the bottom (42) comprises impressed channels (48) on the inside (47), see FIGS. 5 and 6. In the operating state, the bottom (42) of the subshell (41) then permanently abuts against the bottom surface (23) of the mold (21). As illustrated in FIG.

5, the channels (48) can be straight channels (48) parallel to each other, each arranged tangentially to a circle concentric to the central axis (29) penetrating the bottom (42) and the mold (21) in the first operating position, for example. A net-shaped configuration of the impressed channels (48) is also possible. In this case, the subshell (41) can be displaceable parallel to the plane of the bottom surface (23). For example, upon displacement in a displacement direction (12) by half a pitch transverse to the longitudinal direction of the channels, the apertures (25) of the mold (21) are closable on one side in the area of the tip surfaces (28). The filling connection (46) can be provided at the bottom (42) and/or at the edge (43).

The channels (48) impressed into the inside (47) of the bottom (42) can also formed radially, see FIG. 6. Optionally, additional channels (48) are provided that are arranged concentrically about a center of the bottom (42). In this exemplary embodiment, the pitch of the radial channels (48) coincides with the pitch of the apertures (25) of the mold (21). In the operating state, the bottom (42) abuts against the bottom surface (23) of the mold (21). Here, in the initial position, each aperture (25) of the mold (21) shows a radial channel outside the circular channels. The filling connection (46) can be provided in the center of the bottom (42) and/or in the edge region. In case of an arrangement in the edge region, the radial channels are hydraulically connected to each other by a circumferential distribution channel, for example. In this exemplary embodiment, the mold (21) is also displaceable relative to the subshell (41). For example, the mold (21) is pivotable relative to the subshell (41) from the initial position by half a smallest pitch about the central axis (29) in a displacement direction (12) into a second operating position. The smallest pitch is the pitch in which two radials to the center line together enclose the smallest angle through two apertures (25). In the second operating position, all apertures (25) are then closed on one side, e.g. by means of the bottom (42).

Figure 7:
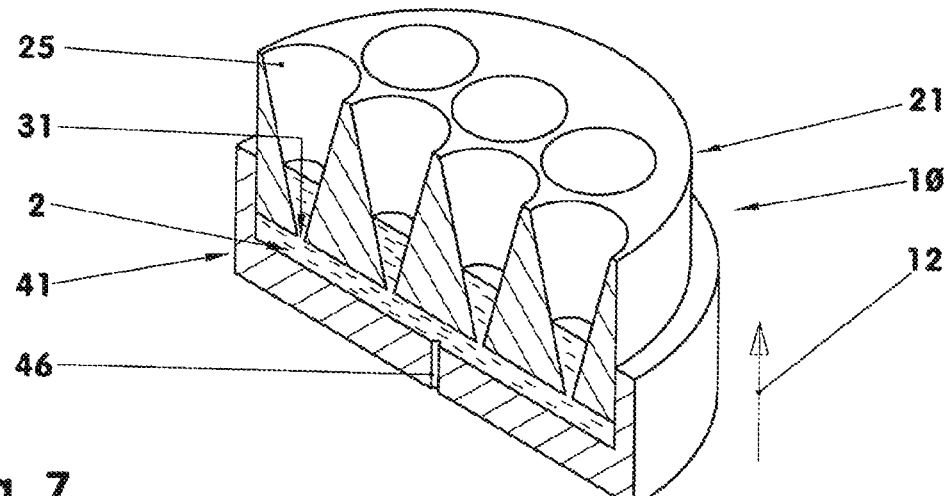
FIG. 7 illustrates an isometric cross-sectional view of an embodiment of the device with an introduction of the active ingredient.

FIG. 7 shows the introduction of a first component (2) into the device (10) shown in FIG. 4. The first component (2) to be introduced is a liquid, for example. The material composition may contain active ingredients or be free of active ingredients. If the first component (2) contains an active ingredient, the active ingredient can be solved, suspended, or embedded in the liquid in the form of microcapsules or particles, respectively. Instead of a liquid first component (2), it is also possible to introduce semi-solid, pasty, or solid masses, substance mixtures, or powders.

The first component (2) is provided in a container, for example, which is mounted to the filling connection (46) at the bottom side. The first component (2) is conveyed into the feed chamber (51) by applying e.g. an external pressure to the flexibly deformable container, for example. The container can also be under positive pressure. The feed chamber (51) is filled with the first component (2). The first component (2) gets from the feed chamber (51) through feed openings (31) into the receptacles (25). In this exemplary embodiment, the feed openings (31) comprise the tip surfaces (28) of the apertures (25).

For example, the surface area of the individual tip surfaces (28) corresponds to the cross-sectional area of the respective feed opening (31). Said cross-sectional area is smaller than or equal to 0.01 square millimeters, for example. The feed openings (31) are produced e.g. by laser, by hot stamping, by micro-milling, by injection molding, by lithography, etc. In this exemplary embodiment, each receptacle (25) has exactly one feed opening (31). All receptacles (25) are filled evenly, for example. Any gas inclusions of the first component (2) rise as gas bubbles and leave the receptacles (25) e.g. through the base surfaces (27). For example, all receptacles (25) are only filled up to a partial level. After filling, the filling level of the first component (2) in the receptacles (25) is between the tip surfaces (28) and the base surfaces (27) in height direction (11). For example, the filling level is at one third of the distance of the two mentioned surfaces as measured from the tip surface (28).

The filling can also be performed such that only individual receptacles (25) of the mold (21) are filled. For example, the feed openings (31) of the other receptacles (25) are e.g. temporarily closed. For example, after said selective filling, the remaining receptacles (25) can remain unfilled or can be filled with another component, e.g. another solution containing an active ingredient. For this purpose, the receptacles (25) that were filled first can then be closed, for example.

The first component (2) can also be introduced into the receptacles (25) by negative pressure in the environment (1) of the mold (21). For example, the e.g. flowable first component (2) is then sucked out of the container which has a high internal pressure relative to the ambient pressure.

Masses that are flowable in a limited manner, semi-solid and solid substance mixtures or powder can also be introduced into the receptacles (25), e.g. by mechanical pressure or a dosage. It is also possible to convey the first component (2) by means of the effect of capillary forces through the feed openings (31) into the receptacles (25).

In the next method step, the feed openings (31) of the receptacles (25) are closed. For this purpose, for example the subshell (41) is displaced relative to the mold (21) in displacement direction (12) until the bottom (42) closes all apertures (25). It is also possible to individually close the feed openings (31) at the bottom surface (23) of the mold (21), to insert a closing plate, to actuate flaps that are hinged via joints, etc. It is also possible to use a pivotable closing plate.

Figure 8:
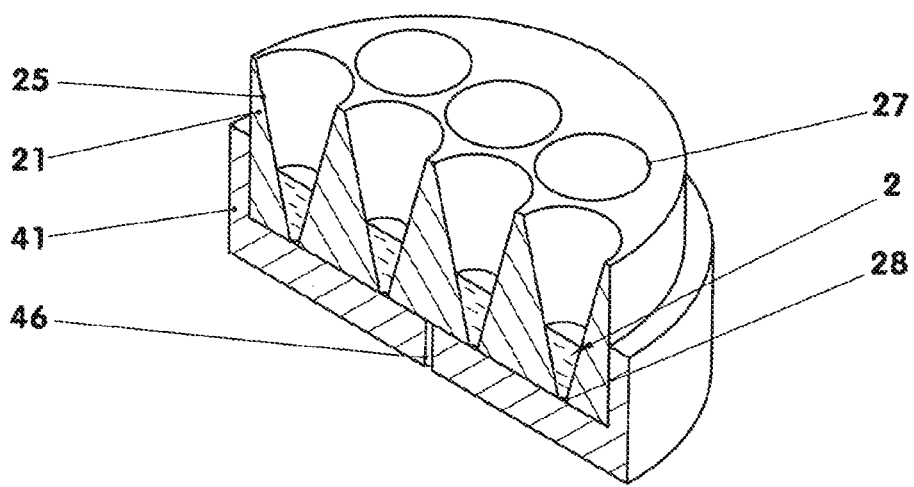
FIG. 8 illustrates an isometric cross-sectional view of an embodiment of the device with a closure of apertures of the mold.

In FIG. 8, the device illustrated in FIG. 4 is illustrated with receptacles (25) that are closed on one side. The connection between the filling connection (46) of the subshell (41) and the receptacles (25) is interrupted. For example, the reservoir can be removed from the filling connection (46). The first component (2) is located in the receptacles (25) that are open to the top. For example, the filling level has at least approximately the same level in all receptacles (25). The receptacles (25) are open at the top surface (22).

Then, the first e.g. liquid component (2) is solidified by drying, for example. The bottom surface (23) of the mold (21) remains closed, the top surface (22) remains open. Drying can be performed at a constant or increased temperature of the environment (1). During drying, evaporation reduces both the mass and the volume of the first component (2) in the receptacles (25). The first component (2) solidifies.

It is also possible to solidify and then optionally dry the first component (2) by a reaction e.g. chemical, thermal, pulse-induced or radiation-induced reaction. Optionally, the method step for solidification of the first component (2) may be omitted.

Figure 9:
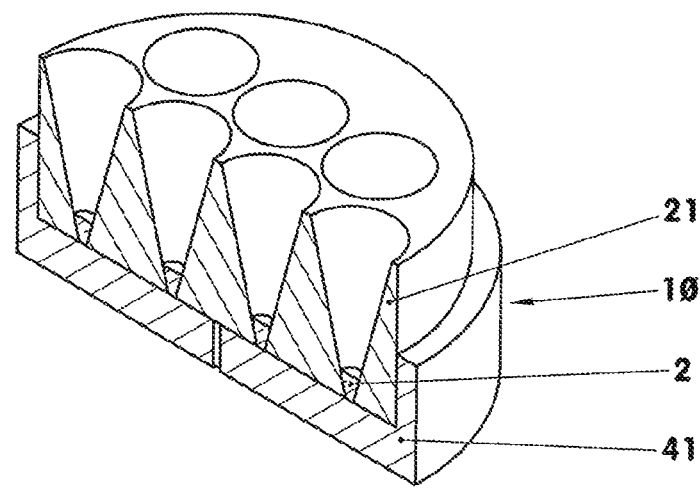
FIG. 9 illustrates an isometric cross-sectional view of an embodiment of the device after drying the first component.

FIG. 9 shows the device (10) with the first components (2) solidified as tips (62). A tip (62) is seated in each receptacle (25) adjoining the tip surface (28) that is flush with the bottom surface (23) of the mold (21), for example. The individual tip (62) is formed to be conical. For example, the lower smallest end surface (63) of the tip (62), which is normal to the center line, is an even circular surface. The largest end surface (64) of the tip (62) facing away from the smallest end surface (32) can be an even circular surface parallel to the smallest end surface (63). However, the largest end surface (64) can also be convex or concave. Furthermore, an irregularly shaped surface can be formed by the drying process or the solidification process, respectively.

The shell surface (65) of the tips (62) is regularly formed in the area adjoining the smallest end surface (63), for example. The shell surface (65) is in full contact with the delimiting surface of the receptacles (25), for example. In the area of the tip (62) adjoining the largest end surface (64), the shell surface (65) can detach from the inner wall of the individual receptacle (25) due to shrinkage upon drying. After drying, the tips (62) are formed in a solid manner.

Figure 10:
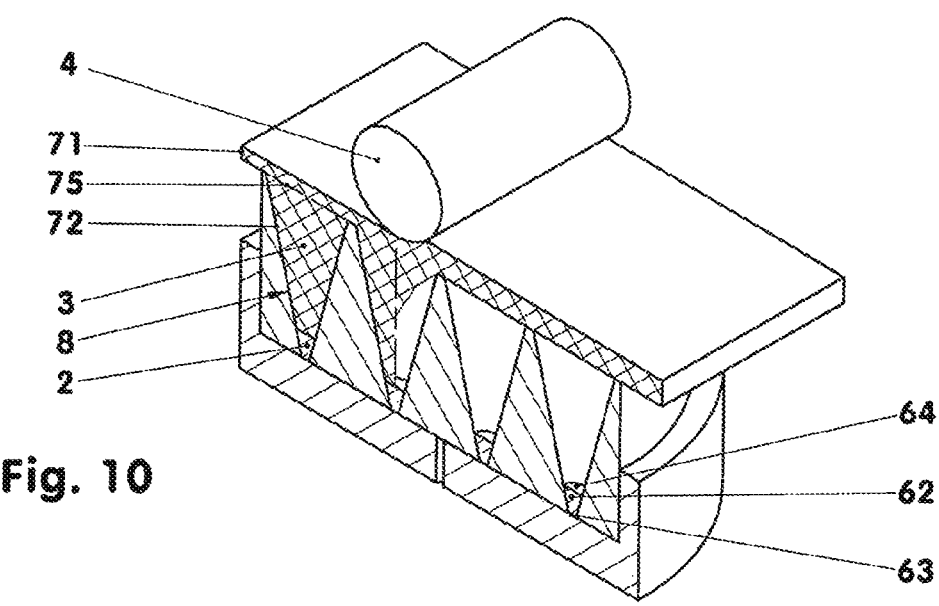
FIG. 10 illustrates an isometric cross-sectional view of an embodiment of the device with a second component.

In a further method step, an additional, e.g. second component (3), e.g. a fill mass, is introduced into the mold (21) and applied to the mold (21), see FIG. 10. Said additional component (3) has a formulation free of active ingredients, for example. Upon application to the mold (21), the additional component (3) can be plastically deformable. For example, the additional component (3) is formed to be toughly deformable. Upon application, the additional component (3) is applied in a thick layer, e.g. up to a thickness of ten millimeters, to the top surface (22) of the mold (21). The additional component (3) is deformable and solidifiable under pressure, for example. The additional component (3) can be applied as a web-shaped or plate-shaped laminate or as powder. Application is also possible as a liquid material by means of a pump. The additional component (3) can also be formed as a ribbon or strip.

The additional component (3) applied to the mold (21) is processed by a compression device (4) in the form of a roller (4), for example. Here, the roller (4) rolls off on the mold (21) and/or on the additional component (3). The additional component (3) is pressed into the receptacle (25). During further overrolling, the second component (3) is solidified both in the receptacles (25) and on the top surface (22) of the mold (21). The second component (3) is pressed in the receptacles (25) onto the respective largest end surface (64) of the individual tips (62). In this joining process, the additional component (3) bonds adhesively to the tips (62), for example. Optionally, an adhesive portion in the additional component (3) can strengthen the join between the additional component (3) and the tips (62). Thus, the fillings (8) of the receptacles (25) each consist of at least the first component (2) and the additional component (3). The additional component (3) is further compressed, e.g. by rolling, wherein the entire additional component (3) is further solidified. The additional component (3) now consists of a support strip (71), e.g. a support plate (71) and conical needle stumps (72). A tip (62) is seated on each needle stump (72). The additional component (3) and the tips (62) are solid and joined together. Respectively one needle stump (72) is connected to one tip (62). Together with the support strip (71) they form a microneedle array (61).

The additional component (3) can already be introduced into the receptacles (25) when being applied to the mold (21). This can be done by casting, injecting, spreading, rolling, etc. Furthermore, stamps be used to solidify the additional component (3). It is also possible to dry the additional component (3) for solidification. Moreover, combinations of the specified methods are possible.

The additional component (3) can also be conveyed into the receptacle (25) directly after the introduction of the first component (2) or simultaneously with the introduction of the first component (2). In this case, there is no separate solidification or drying of the first component (2), for example.

The application of more than two components is also possible. Here, the needle stumps (72) can consist of the additional component (3), for example. The support strip (71) is then a ribbon joined with the needle stumps (72), for example.

Figure 11:
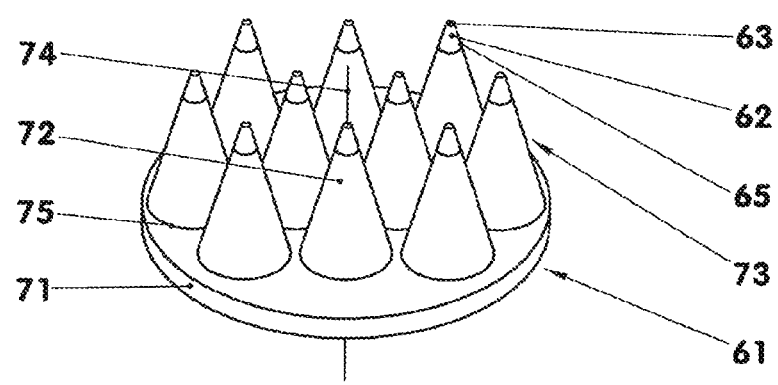
FIG. 11 illustrates an isometric view of an embodiment of a microneedle array.

After solidification of the additional component (3), the microneedle array (61) can be removed from the mold (21). FIG. 11 shows the microneedle array (61) after demolding. It consists of the support strip (71) and a plurality of rigid needles (73) which all point towards the same direction, for example. Each needle (73) comprises a needle stump (72) formed on the support strip (71) in a needle connection cross-section (75), on the side of which facing away from the support strip (71) a tip (62) is joined. In the exemplary embodiment, all needles (73) are perpendicular to the support strip (71). The support strip (71) can be configured to be elastically deformable. All needles (73) have identical geometric dimensions, for example. The end surface of each needle (73) facing away from the support strip (71) is formed by a smallest end surface (63) of a tip (62). In this exemplary embodiment, said smallest end surface (63) is normal to a center line (74) of the individual needle (73).

In the exemplary embodiment, the support strip (71) is formed as a disc having a circular cross-section. The support strip (71) projects beyond the envelope contour of the needle (73) in the needle connection cross-section (75). Regardless of the design of the mentioned envelope contour of the needle (73), the support strip (71) can comprise a circular, elliptical, rectangular, triangular, etc. cross-section in a plane normal to the longitudinal direction of the needles (73).

The individual needles (73) of the solidified fillings (8) can first also be produced without connection through the support strip (71). In order to remove the needles (73) from the receptacles (25), a support strip (71) is then connected to the needles (73), for example. For this purpose, the support strip (71) is joined adhesively with the needles (73) at the needle connection cross-section (75), for example. The support strip (71) can be configured as a support plate, a support layer, e.g. as a polymeric adhesive film, as an adhesive tape, etc. In this case, the microneedle array (61) removed from the device (10) consists of at least two needles (73) and the support strip (71).

After removal of the microneedle array (61) from the device (10), the latter can be re-used, for example. After cleaning the device (10), a further microneedle array (61) is produced by means of said device (10), for example. This repeated production is performed as described above.

Figure 12:
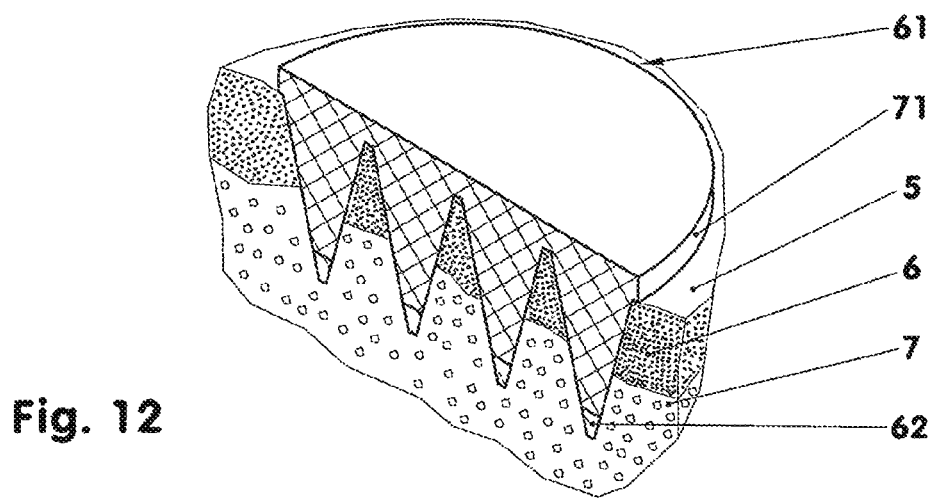
FIG. 12 illustrates an isometric cross-sectional view of an embodiment of the microneedle array upon application on skin of a patient.

In FIG. 12, the application of the microneedle array (61) is illustrated. The microneedle array (61) is placed with the support strip (71) on the skin (5) of a patient. The support strip (71) with the needle stumps (72) that are free of active ingredients, for example, ensure the geometric alignment and fixation of the microneedles (61). For example, the microneedle array (61) can additionally be fixed by an adhesive tape. Here, the microneedle array (61) can be formed as a patch. The rigid needles (73) penetrate the callus (6) and project into at least one further skin layer (7). In doing so, the needles (73) are not plastically deformed and do not break, for example. After penetration, the tips (62) are located entirely in the skin layer (7) below the callus (6), for example. The active ingredient is located in the tips (62) in a quantitatively and spatially defined manner, for example. Due to the environmental conditions in the skin layer (7), the active ingredient is delivered to the skin layer (7). In doing so, the tips (62) can decay. For example, the tips (62) dissolve when absorbing liquid in the skin layer (7). Thus, the active ingredient is delivered to the body of the patient.

Depending on the wearing period intended according to the application, e.g. after ten minutes, the microneedle array (61) can be removed from the skin (5) of the patient.

Figure 13:
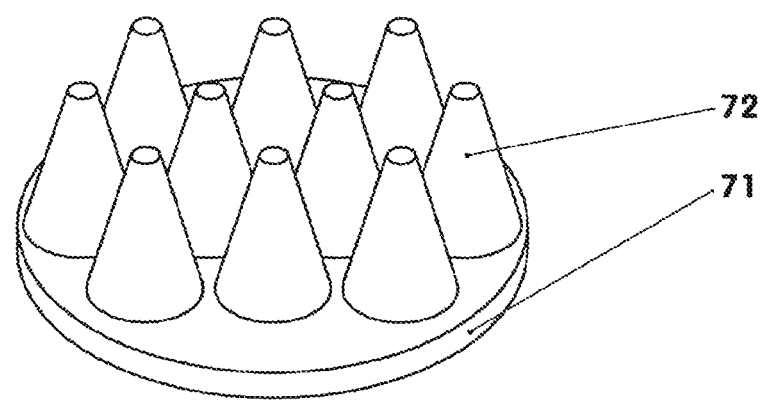
FIG. 13 illustrates an isometric view of an embodiment of the microneedle array after removal.

FIG. 13 shows the microneedle array (61) of FIG. 12 after removal from the skin (5) of the patient. Now, the microneedle array (61) only consists of the solidified, insoluble additional component (3) or the support strip (71), respectively, and the needle stumps (72) hanging thereon. These used microneedle arrays (61) are secured from unintentional re-use due to the missing tips (62). They can be disposed. Thus, among other things, safety for the patients is ensured.

It is also possible to produce the needle tips (62) as well as the needle base or needle butts and the support strip (71) of soluble components or substance mixtures.

Alternatively, it is also possible to produce the needle tips (62), the needle base, and the support strip (71) of insoluble components or substance mixtures. For example, one or several substances included for therapeutic and/or diagnostic application are delivered to the surrounding skin layer after swelling with moisture absorption.

The needle tips (62) can also consist of a less rapidly soluble component, while the needle base and support plate (71) consist of a rapidly soluble component. This leads to a change in the release rate of active ingredients from the respective component.

In case of a device (10) with a lateral filling of active ingredient, the subshell (41) illustrated in FIG. 3 can be used, for example. The first component (2) is then stored in a container laterally flanged to the subshell (41). For example, an ambient pressure prevails in the inside of the container. When opening a container valve, the liquid first component (2) stored in the container flows to the subshell (41). From there, the first component (2) rises through the tip surfaces (28) forming the feed openings (31) into the receptacles (25). The rise continues until the level in the receptacles (25) is at least as high as in the container. Optionally, the level of the liquid in the receptacles (25) may exceed the level of the second component (2) in the container due to capillary effects.

Figure 14:
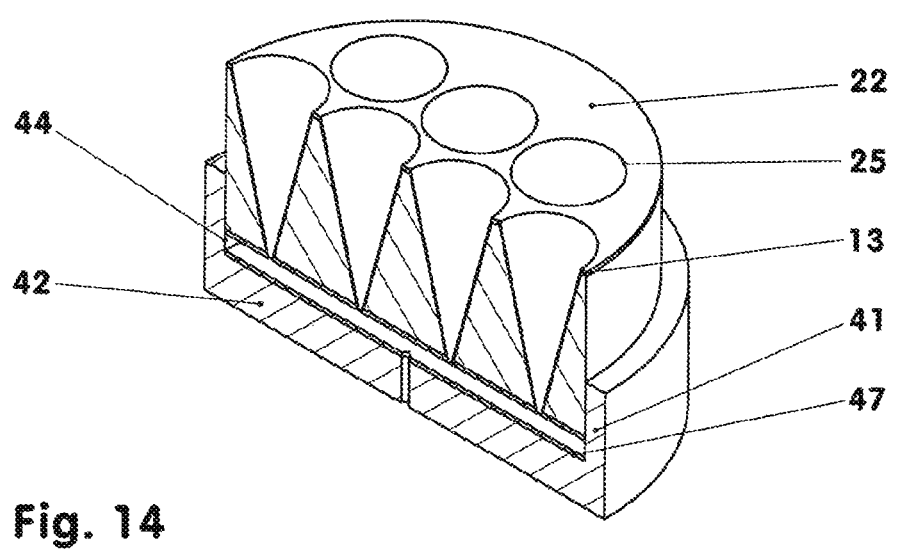
FIG. 14 illustrates an isometric cross-sectional view of an embodiment of the device with coated surfaces.

FIG. 14 shows a device (10) with surfaces that are modified area by area. In the mold (21), the inner surfaces of the receptacles (25), the top surface (22) and the bottom surface (23) are configured such that said surfaces are non-adhesive with respect to the material of the tips (62) and the additional component (3). The static friction of the mentioned material with respect to the mold (21) is reduced as compared to a non-modified surface. For example, in the subshell (41), the inner side (47) of the bottom (42) facing the mold (21) and the inner surface (44) of the edge (43) are configured such that the adhesion of the initial material of the tips (62) is prevented.

Adhesion can be reduced by a coating (13) of the mentioned surfaces, by application of a release agent and/or by mechanical processing of the surfaces. In this respect, the applied methods and coating materials and/or release agents may vary. The surfaces that only come into contact with the additional component (3) may be treated differently than the surfaces that only come into contact with the material of the tips (62) during production of the microneedle array (61).

In case of a coating (13) of the surfaces, the coating (13) can consist of polytetrafluorethylene, polyethylene, polypropylene, etc. For example, a polysorbate or another oily release agent can be used as a release agent applied to the mentioned surfaces.

If the surfaces are treated mechanically, the surface roughness can be reduced, e.g. by electropolishing, corona treatment, laser polishing, etc. All these measures reduce losses during dosage of the microneedle array (61) and facilitate damage-free removal of the microneedle array (61) from the mold (21).

Figure 15:
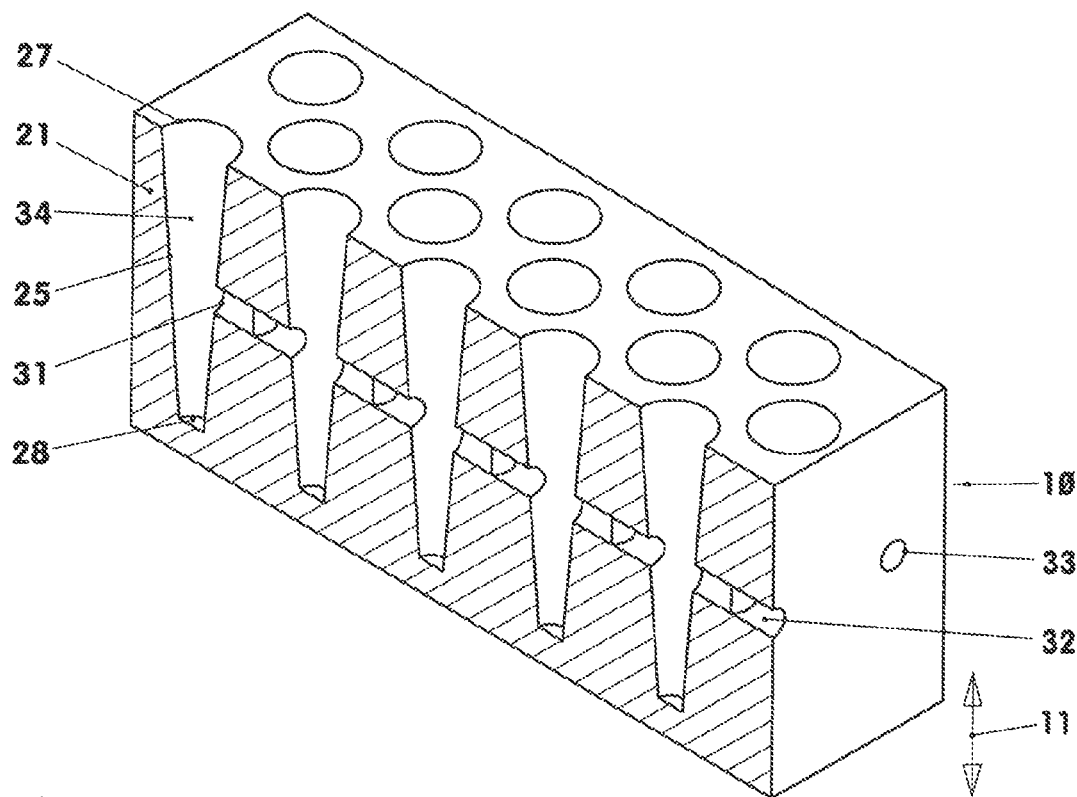
FIG. 15 illustrates an isometric view of an embodiment of the device with lateral feed openings.

FIG. 15 shows an isometric sectional view of a device (10) without subshell (41). The device (10) consists of a cuboid mold (21), for example. The receptacles (25) are arranged in several rows offset to one another. The arrangement and design of the receptacles (25) largely corresponds to the arrangement and design of the receptacles (25) described in connection with the aforementioned exemplary embodiments. The receptacles (25) are closed at the respective tip surfaces (28).

Feed openings (31) open into the inner shell surfaces (34) of the receptacles (25). The feed openings (31) are located below the base surfaces (27). For example, the feed openings (31) are arranged, starting from the tip surfaces (28), in the lower half of the height of the receptacles (25) in height direction (11). An arrangement in the lower third or in the lower fifth of the height is also possible. The cross-section of the individual feed opening (31) corresponds to the surface of the individual tip surface (28), for example.

The feed openings (31) are connected by feed channels (32) to feed connections (33) accessible from the outside of the mold (21). For example, a reservoir, which is not illustrated here, is connected to the feed connections (33). For example, said reservoir is configured as explained in connection with the previously described exemplary embodiments. The net of e.g. intersecting feed channels (32) forms a feed chamber (51), for example. It is also possible to arrange all feed connections (33) on an exterior of the mold (21).

Figure 16:
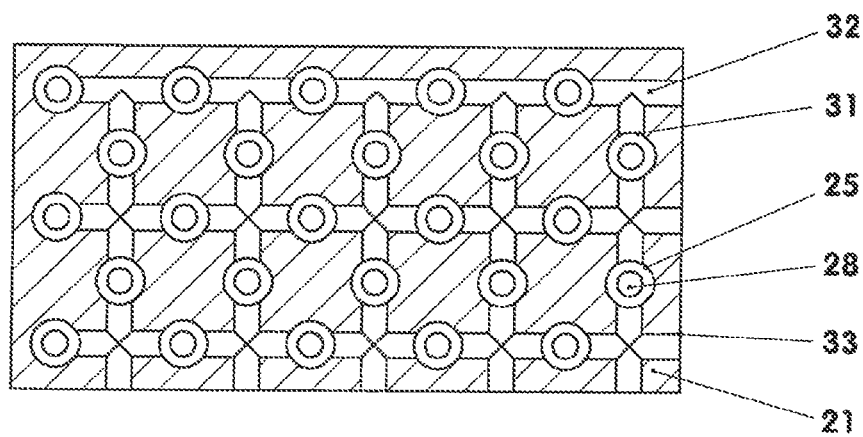
FIG. 16 illustrates a cross-section of the device in FIG. 15 in the area of the feed channels.

FIG. 16 shows a sectional view of such a mol (21) with inside feed channels (32). The sectional plane is horizontal, for example, the sectional plane is parallel to the plane of the bottom surface (23). The feed connections (33) are located at two lateral surfaces of the mold (21), for example. The feed channels (32) connect the individual receptacles (25) to each other.

After connecting the mold (21) to the reservoir, the first component (2) flows through the feed channels (32) into the receptacles (25). Due to the receptacles (25) communicating with each other, all receptacles (25) are filled to the same level. For example, when the first component (2) is filled without pressure, the filling level of the receptacles (25) lies within the cross-sectional area of the feed openings (31) and the feed channels (32) aligned therewith. The first component (2) can be solidified separately. For this purpose, the connection of the first component (2) to the feed opening (31) is separated, for example. The remaining liquid stock from the feed chamber (51) flows along the feed channels (32) into the receptacles (25). The feed channels (32) are emptied, for example.

The second component (3) is filled into the receptacles (25) as described above. For example, the additional component (3) and the support strip (71) are then solidified. In this exemplary embodiment, the fillings (8) can also be solidified together. It is also possible to affix the support strip (71) onto the needles (73) after the fillings (8) have solidified, or to connect the support strip (71) to the needles (73) in a form-fitting or materially bonded manner.

In this exemplary embodiment, the additional component (3) can also be fed through filling openings of the inner shell surfaces (34) of the receptacles (25), wherein the filling openings are located in height direction (11) between the feed openings (31) and the base surfaces (27).

For example, the several jointly produced microneedle arrays (61) are removed from the mold (21) as described above. In doing so, remaining connection between the fillings (8) and the feed channels (32) can be separated, if necessary. The mold (21) can be used as a reusable or as a disposable mold (21), e.g. as a dead mold (21).

The individual microneedle arrays (61) are applied as described above.

The specified exemplary embodiments can also be combined with each other.

The invention claimed is:

1. A method for producing microneedle arrays in a mold comprising:
    providing a mold comprising a plurality of receptacles that taper from an upper base surface to a lower tip surface; and
    feeding a first component through the tip surfaces, or through a receptacle inner shell surface, into at least two receptacles through a feed opening that is spaced apart from the base surface,
    wherein the at least two receptacles are filled with an additional component from above the feed opening, wherein the fillings of at least the two receptacles are formed of at least the first component and the additional component, wherein the fillings of at least the two receptacles are connected to one another above the base surfaces, and wherein, after the first component and the additional component have solidified, the microneedle array comprising the fillings that have solidified to form needles is removed from the mold.

2. The method according to claim 1, wherein, after feeding the first component, at least a plurality of tip surfaces are closed by a subshell that is movable relative to the mold.

3. A device for producing microneedle arrays by means of a method according to claim 1, comprising a mold, wherein the mold comprises a plurality of receptacles that taper from an upper base surface to a lower tip surface, wherein each receptacle comprises a feed opening that is spaced apart from the base surface, and wherein the feed opening of each receptacle comprises the tip surface of the receptacle.

4. The device according to claim 3, wherein the feed opening connects the receptacle to a feed chamber forming a reservoir.

5. The device according to claim 3, wherein the surface area of a cross-sectional area of an individual feed opening is smaller than or equal to 0.01 square millimeters.

6. The device according to claim 3, wherein the tip surfaces lie in a first plane.

7. The device according to claim 3, wherein the tip surfaces are closable.

8. The device according to claim 3, further comprising a compression device that is arranged above the mold.

9. The device according to claim 3, wherein the surfaces of the top surface, the bottom surface and the receptacle of the mold are configured to be non-adhesive in at least some areas.

10. A device for producing microneedle arrays by means of a method according to claim 1, comprising a mold, wherein the mold comprises a plurality of receptacles that taper from an upper base surface to a lower tip surface, wherein each receptacle comprises a feed opening that is spaced apart from the base surface, and wherein the surface area of a cross-sectional area of an individual feed opening is smaller than or equal to 0.01 square millimeters.

* * * * *